United States Patent
Gordon

(10) Patent No.: US 8,524,759 B2
(45) Date of Patent: Sep. 3, 2013

(54) PHENYLBUTAZONE CARRIER FORMULATION SHOWING INCREASED BIOACTIVITY IN ANIMALS

(76) Inventor: Douglas J. Gordon, Pleasant Grove, UT (US)

( * ) Notice: Subject to any disclaimer, the term of this patent is extended or adjusted under 35 U.S.C. 154(b) by 0 days.

(21) Appl. No.: 13/543,948

(22) Filed: Jul. 9, 2012

(65) Prior Publication Data

US 2012/0277278 A1 Nov. 1, 2012

Related U.S. Application Data

(63) Continuation-in-part of application No. 12/608,913, filed on Oct. 29, 2009, now abandoned.

(60) Provisional application No. 61/227,282, filed on Jul. 21, 2009.

(51) Int. Cl.
| A61K 31/415 | (2006.01) |
| A61K 9/58 | (2006.01) |
| A61K 9/60 | (2006.01) |
| A61K 9/68 | (2006.01) |
| A61K 9/26 | (2006.01) |

(52) U.S. Cl.
USPC ........... 514/404; 424/419; 424/484; 424/485; 424/486; 424/487; 424/488; 424/408; 424/417

(58) Field of Classification Search
USPC ................. 514/404; 424/419, 484, 485, 486, 424/487, 488, 408, 417
See application file for complete search history.

(56) References Cited

U.S. PATENT DOCUMENTS

| 3,927,213 A | 12/1975 | Lippmann |
| 3,957,803 A | 5/1976 | Bodor et al. |
| 4,455,298 A | 6/1984 | McFarlane et al. |
| 4,952,402 A * | 8/1990 | Sparks et al. ................. 424/419 |
| 5,240,922 A | 8/1993 | O'Neill |
| 6,022,563 A | 2/2000 | Gordon |
| 6,552,063 B2 | 4/2003 | Green |
| 2005/0129781 A1 * | 6/2005 | Skiendzielewski et al. .. 424/601 |
| 2005/0152975 A1 | 7/2005 | Nakagami et al. |
| 2005/0249806 A1 | 11/2005 | Proehl et al. |
| 2011/0021591 A1 * | 1/2011 | Gordon ........................ 514/404 |

* cited by examiner

*Primary Examiner* — Ernst Arnold
*Assistant Examiner* — Hong Yu
(74) *Attorney, Agent, or Firm* — Brett Peterson; Pate Peterson PLLC

(57) ABSTRACT

An improved phenylbutazone carrier composition provides increased palatability to horses. Additionally, the composition improves the bioavailability of the phenylbutazone and thus increases the horse's blood plasma levels of the medicine for the same effective dosage of the medicine.

20 Claims, 1 Drawing Sheet

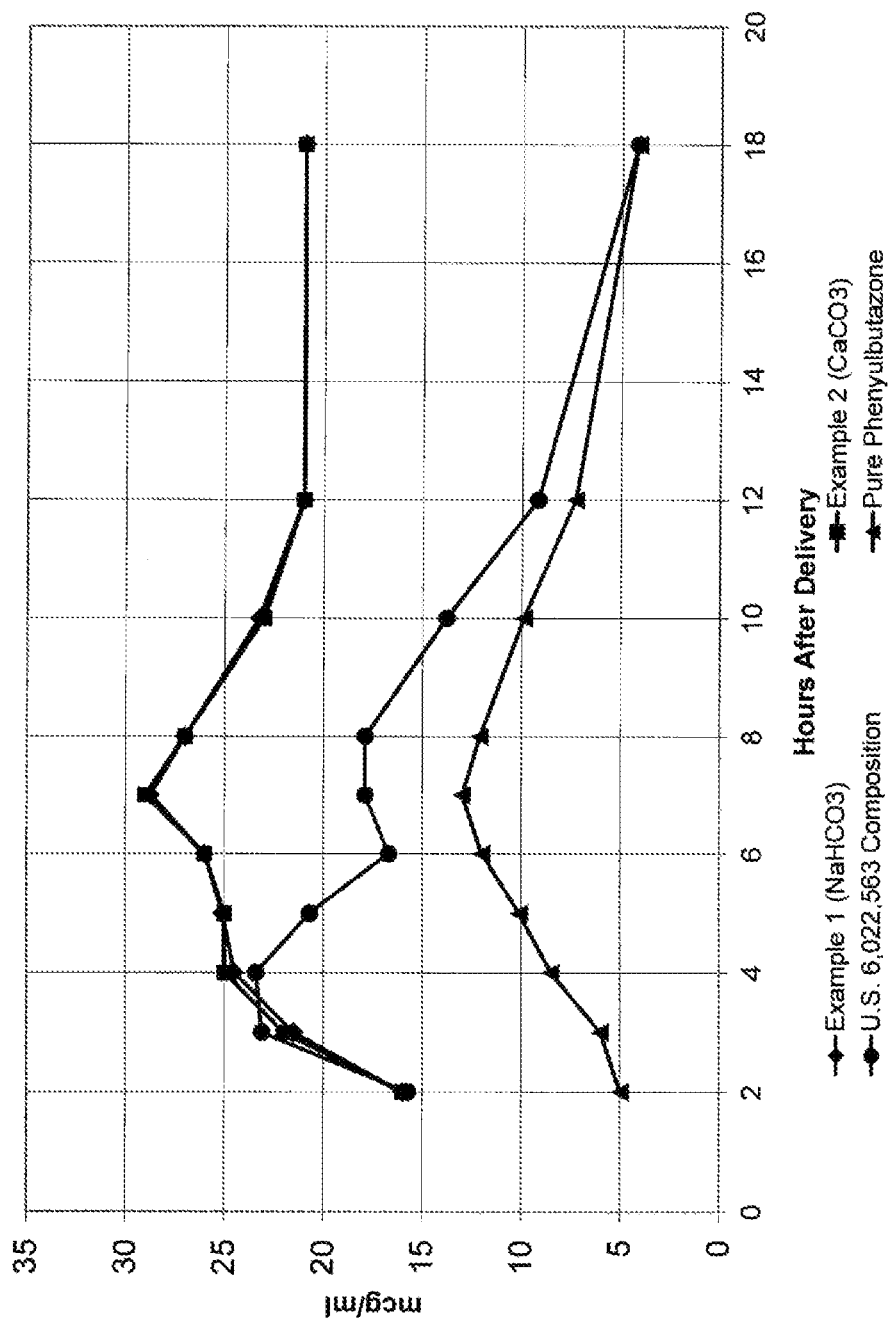

PHENYLBUTAZONE CARRIER FORMULATION SHOWING INCREASED BIOACTIVITY IN ANIMALS

PRIORITY

The present application is a continuation in part application of U.S. application Ser. No. 12/608,913, filed Oct. 29, 2009 now abandoned, which is herein incorporated by reference in its entirety, and which claims the benefit of U.S. Provisional Application Ser. No. 61/227,282, filed Jul. 21, 2009, which is herein incorporated by reference in its entirety.

THE FIELD OF THE INVENTION

The present invention relates to providing phenylbutazone to horses. More specifically, the present invention relates to an improved carrier formulation for delivery of phenylbutazone and functional homologues thereof. The carrier is more palatable to horses than previous phenylbutazone formulations and provides improved absorption into the horse's blood stream.

BACKGROUND

Phenylbutazone, is one of the most popular and useful non-steroidal anti-inflammatory veterinary pharmaceuticals. It is typically the drug of choice for equine treatment when an illness or injury necessitates the use of a painkiller or anti-inflammatory medication. Phenylbutazone treats joint deterioration, swelling and inflammation from injuries, founder, fevers, and various other pains experienced by horses.

While phenylbutazone has been used to treat horses for more than thirty years, the administration of phenylbutazone persists in being the source of many problems. Phenylbutazone has a bitter taste, and is thus difficult to administer orally, but oral administration remains the desired mode of administration. The horses often reject the bitter drug, which leads to inconsistent dosages and difficulty in administering the drug.

Phenylbutazone is typically available to horse owners and veterinarians in one-gram tablets for oral administration. Horses do not willingly eat phenylbutazone tablets. Absent physical force, most horses will not swallow phenylbutazone tablets due to their bitterness. Thus, administration of these tablets involves first catching the horse and, depending on the individual personality and training of the horse, applying various degrees of restraints. Restraints range from a halter to prevent bobbing and weaving of the head, to more extreme measures that prevent rearing and kicking.

Horse owners and veterinarians have developed several means for the actual delivery of phenylbutazone to horses. In simple cases the tablets are crushed and mixed with the horse's food. This method is problematic because the crushed tablets do not adhere to the horse's food. Powder or granules sift to the bottom of the feeder as the horse eats. The amount of sifting varies with each administration and results in inconsistent dosages or diet problems due to the addition of feed to administer the remaining medication.

Some horses reject the grain and drug mixture altogether, requiring the additional step of mixing the crushed tablet with syrup or molasses before adding the bitter drug to the horse's feed. This method is problematic for several reasons. Syrup and molasses are very sticky, and the mixing process leaves a mess in the surrounding area as well as in the mixing container and feed trough or dish. This can result in a loss of medication and an inconsistent dose. In addition, the phenylbutazone is insoluble in syrup and molasses making it impossible to obtain a homogeneous mixture. If the mixture is not immediately administered to the horse, the phenylbutazone settles resulting in an inconsistent dosage or additional mixing requirements. Encapsulation of the crushed tablet matter by the syrup or molasses also hinders the speed at which digestive fluids can interact with the phenylbutazone and, consequently, blood absorption of phenylbutazone is delayed through the digestive process.

The various method of administering phenylbutazone to horses are unpleasant for the horse and the person, and can result in injury if the person administering the drug is bitten, pawed or stepped on by a stubborn horse. Because the medicine is bitter, a horse will continue to reject the medicine with increasing intensity over time. Ultimately, it becomes difficult or impossible to catch the horse three times a day for delivery of the drug and, if caught, the horse attempts to reject the medicine both before and after it is delivered.

The described administration problems with phenylbutazone would be merely inconvenient, except that they, in turn, cause serious problems, which are related to effective dosages. The drug is intended to control potentially chronic inflammation and pain, which can result in permanent soft tissue lesions, such as scarring of other fibroid tissue growth, as a consequence of long term chronic inflammation cycles. The drug provides relief from chronic cycles of inflammation and pain, and eventually facilitates increased range of motion without permanent loss of function. Thus, it is important to provide a method of administration that avoids peaks and valleys in the blood concentration levels of phenylbutazone arising from inconsistent dosage due to rejection or an inability to catch the horse for administration of the drug.

An important factor to consider in the delivery of phenylbutazone, in addition to methods for oral administration of the drug, is the speed at which the drug is absorbed into the horse's blood. Inflammation and pain are more easily relieved when effective treatment concentrations are attained more quickly. This is especially true when the inflammation is potentially associated with hemorrhaging due to soft tissue injury. Maintaining the proper blood concentration level, timing, and diet are critical to the effectiveness of the drug. Even so, it is commonly understood that mixing a drug with a carrier, such as a nutritional base for delivery of the drug, has the disadvantage of slowing down the blood absorption rate.

While a veterinarian should make the determination on an individual basis, a moderate dose for a 1000 pound horse is 1-2 grams or 5-10 cc per administration. Oral administration of phenylbutazone is slow to take effect, requiring 3-5 hours to achieve an effective concentration level. Three dosages per day should be administered to maintain the proper blood concentration level. However, due to the problems with oral administration, most horse owners and veterinarians settle for a double or sometimes only a single dosage per day, as opposed to the ideal triple dosage. Administration and dosage problems are compounded where prolonged treatments are required for treatment of chronic soft tissue injuries, and these problems can result in significant health effects to the horse and cost burden on the owner.

Some efforts have been made to improve the delivery of phenylbutazone to horses. U.S. Pat. No. 6,022,563 describes carrier formulations which ease administration of the medicine to the horse. While the formulations provided improved the ability to induce the horse to eat the medicine, there remained some difficulty in administering the medicine to the horse. Additionally, the carrier formulations provided showed little increase in the horse phenylbutazone blood concentration as compared to pure phenylbutazone tablets.

Because of the difficulty in administering phenylbutazone and the rejection of the same by horses discussed above, it would be desirable to have a more easily administered formulation and to achieve increased blood concentrations in horses.

Therefore, there is a need for an improved carrier formulation of phenylbutazone that is more palatable to horses than prior formulations, that is easily administered in a proper dosage without special skills or alteration from its manufactured state, and provides quicker absorption into the bloodstream and increased blood concentrations.

SUMMARY OF THE INVENTION

It is an object of the present invention to provide an improved phenylbutazone bearing formulation for administration to animals, including horses.

The present invention overcomes the problems that are outlined above and advances the art by providing an improved carrier formulation for administering phenylbutazone in a palatable medium to horses. The carrier formulation comprises a powdered carrier base including a flavoring agent, a sweetener, and an anti-caking agent mixed with a therapeutically effective amount of phenylbutazone. Additionally, the present carrier formulation includes a buffer, helping to improve the palatability and bioavailability of the drug. The present phenylbutazone mixture is more palatable to horses than the prior art carrier formulations, and also results in improved levels of phenylbutazone in the horse's blood.

These and other aspects of the present invention are realized in a phenylbutazone formulation as shown and described in the following figures and related description.

BRIEF DESCRIPTION OF THE DRAWINGS

Various embodiments of the present invention are shown and described in reference to the numbered drawing wherein:

FIG. 1 shows a graph illustrating the blood levels of phenylbutazone in a horse as achieved by the present invention.

It will be appreciated that the drawing is illustrative and not limiting of the scope of the invention which is defined by the appended claims. The embodiments shown accomplish various aspects and objects of the invention. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Phenylbutazone is known and is described in U.S. Pat. No. 2,562,830. Phenylbutazone is also known as 4-butyl-diphenyl-3,5-pyrazoidinedione, benzone, butadione, intrabutazone, and numerous other common names. Phenylbutazone is widely understood to be an effective veterinary anti-inflammatory and analgesic agent in treating inflammation in horses and other animals.

According to the present invention, the phenylbutazone formulation includes phenylbutazone, flavoring, anti-caking agent, saccharine, aspartame, sucralose, and sodium bicarbonate or calcium carbonate. The formulation is discussed in additional detail below.

The flavoring agent is an inactive ingredient, and is typically an artificial flavoring. Flavor additives used in the flavoring agent may also be products from a natural material. Although a variety of flavor additives are palatable to horses including but not limited to, cinnamon, strawberry, carrot, orange, or apple, it has found artificial green apple flavoring, such as that which is commercially available from BFI Innovations of Elgin, Ill. to be the most palatable to the broadest range of horses.

Artificial sweeteners provide the advantage that, unlike natural sugars, they do not promote significant tooth decay and contribute few if any calories to the foods they sweeten. Additionally, it has been found that the particular sweetener combination disclosed herein has improved the palatability of the phenylbutazone formulation over the prior art carrier formulations. The particular formulation disclosed herein has been shown to improve the levels of phenylbutazone in a horse in addition to improving the ease with which the phenylbutazone may be administered to the horse.

Although beneficial, the anti-caking agent is not a necessary ingredient to the carrier formulation of the present invention. The anti-caking agent is utilized for the practical requirement of improving the manufacturing process. The preferred anti-caking agent is silica (silicon dioxides sold under the trade name Flogard, an example of which can be purchased from Pharmatech Inc. The anti-caking agent improves the manufacturing process by preventing clotting and balling of the product typically caused by the tacky nature of the flavoring ingredients. It should also be noted that, while the anti-caking agent silica dioxide is added to the carrier formulation to improve manufacturing, some additional anti-caking agents may present as sub-ingredients in some of the flavoring ingredients. For example, calcium silicate is often found as a sub-ingredient of the Fresh Green Apple flavoring ingredient.

The particular phenylbutazone formulation disclosed herein has proved advantageous over prior art formulations. For example, while the carrier formulation discussed in U.S. Pat. No. 6,022,563 shows a slightly faster initial delivery speed as compared to pure phenylbutazone, the '563 formulation shows rates of absorption and metabolization of the phenylbutazone over subsequent intervals which is approximately equivalent to that of delivery of pure phenylbutazone, resulting in substantially the same biological effect of the phenylbutazone alone. The present phenylbutazone formulation, however, shows improved delivery speed as well as improved absorption and metabolism of the phenylbutazone, resulting in higher blood concentrations as compared to phenylbutazone tablets. Thus, the present formulation achieves improved biological effectiveness of the phenylbutazone in addition to improved ease of administration to the horse.

The respective ingredients of the carrier formulation are typically provided as a solid, powder, or particulate at room temperature, so that mixing of the materials results in a finely divided powder. The resulting powder has an electrostatic affinity for the cellulosic substances that horses eat, making it easier to mix the phenylbutazone composition into horse feed.

The carrier formulation is produced by blending the ingredients to achieve a homogeneous mixture. A suitable weight proportion of phenylbutazone to achieve the advantages of the invention may be in the range of 70% to 90% of the total formulation weight, with a more preferable range being 85% to 90%. The formulation preferably has between 1% and 5% flavoring, about 3.5% saccharine, about 1% aspartame, and between 1.8% and 3.6% sucralose.

The carrier formulation of the present invention is administered to horse orally in its raw form or as a feed supplement by spreading it over conventional feed components, including but not limited to, grain, hay, oats, barley, corn and so on. Advantageously, the sweetener ingredients typically provide the carrier formulation with an inherently tacky property, such that the carrier formulation adheres to feed when it is administered as a feed supplement. Thus, product is not lost due to sifting as the horse eats. Horses consider that phenylbutazone delivered with the carrier formulation as a treat, and they aggressively ingest it Example 1

Example 1 describes a preferred product formulation for the present invention, as well as the mixing and administration of the product.

During the first stage of preparation, seven individual batches of product were mixed, each having a total weight of 115 kilograms. A 200 kilogram stainless steel blending mixer, commonly known in the art as a V-shaped blender, was used to mix each batch. Before each batch was mixed the blending mixer was sterilized by thoroughly wiping with a sterile cloth soaked in rubbing alcohol. During the second stage of preparation, the seven individual batches were combined and mixed in a 1000 kilogram stainless steel V-shaped blending mixer to produce the finished product.

Each of the seven batches produced during the first stage of preparation consisted of: 100 kilograms of phenylbutazone, 4 kilograms of saccharine, 3 kilograms of Fresh Green Apple Flavor, 2 kilograms of Aspartame, 2 kilograms of sodium bicarbonate, and 4 kilograms of FloGard. The ingredients for a single batch were weighed and placed in the 200 kilogram blending mixer and blended for a period of 15 minutes. After 15 minutes of blending, the batch was removed from the 200 kilogram blending mixer and weighed to confirm any product loss. An average of 2% was lost do to coating the machinery. After weighing, the batch was placed into a 1000 kilogram blending mixer, but was not mixed until all seven batches from the first stage of preparation were added to the 1000 kilogram mixer.

During the second stage of production the seven batches were blended in the 1000 kilogram blender for a period of 20 minutes to produce 789 kilograms of finished product (accounting for the lost material in blending in the first stage). After blending, the finished product was removed and weighed to confirm any product loss. Approximately 1% was lost. After weighing, the product was tested for bacteria and continuity before packaging in individual doses. The packaged product contained 1 gram of phenylbutazone, 0.04 gram of Saccharine, 0.03 gram of Fresh Green Apple Flavor, 0.02 gram of Aspartame, 0.02 gram of sodium bicarbonate, and 0.04 gram of FloGard, per 3.5 cc spoonful of powder.

Bioequivalence Test

The above product mixture was tested for bioequivalency as follows. Three healthy mature geldings and two non-pregnant mares aged 3-15 years with similar weights were chosen for a bioequivalence test. The bioequivalence test was designed to determine the difference in blood plasma absorption between commercially available phenylbutazone tablets and the inventive product mixture described above.

Two weeks prior to the test, the horses did not receive any form of medication; however, all horses were up to date on their vaccinations. At five o'clock p.m. the evening before the test, each horse was fed a normal meal consisting of 1 gallon of grain with fourteen percent protein, and ten pounds of alfalfa hay. During the test each horse was stabled separately and had access to drinking water at all times. On test day, each horse was fasted until administration of the test product, and then given a normal meal consisting of one gallon of grain with fourteen percent protein and ten pounds of alfalfa hay five hours post dosing and at twelve and one-half hours after administration.

The morning of the test, 4.60 grams of the product from example one containing a total of four grams of phenylbutazone, was added to one half gallon of grain with fourteen percent protein by lightly stifling. Each horse was given 15 minutes to consume the grain. All five horses consumed their grain during this allotted time. Each of the five horses followed this procedure.

Two hours following administration a 4.5 cc blood sample was taken from each of the five horses. Thereafter, additional 4.5 cc blood samples were taken at half-hour intervals until the sixth hour. After the sixth hour 4.5 cc blood samples were taken hourly until the eighth hour. After the eighth hour 4.5 cc blood samples were taken at twelve and one-half hours, sixteen hours, and eighteen hours. The blood samples were taken with a 20 gauge one inch needle and promptly put into a green CST Lithium Heparin tubes and cooled in ice water at 36 degrees F. When each sample was collected, the blood sample was spun to separate the blood plasma from each sample. The separated blood plasma was placed in a freezer for twenty-four hours at 20 below zero.

After twenty-four hours, the blood plasma was thawed to room temperature and phenylbutazone levels were quantified for each sample by a validated HPLC method. The average phenylbutazone level for the five horses at each of the sampling time intervals are given in FIG. 1.

Two weeks later after completing a wash out period, the same three healthy mature geldings and two non-pregnant mares aged 3-15 years with similar weights were used for a cross over bioequivalence test. This bioequivalence test was to determine the concentration levels in blood plasma absorption of commercially available phenylbutazone tablets.

Two weeks prior to the test, the horses did not receive any form of medication, however all horse were up to date on their vaccinations. At five o'clock p.m. the evening before the test, each horse was fed a normal meal consisting of 1 gallon of grain with fourteen percent protein, and ten pounds of alfalfa hay. During the test each horse was stabled separately and had access to drinking water at all times. On test day, each horse was fasted until administration of the test product (4 grams of crushed active ingredient phenylbutazone in tablets), and then given a normal meal consisting of one gallon of grain with fourteen percent protein and ten pounds of alfalfa hay five hours post dosing, and at twelve and one-half hours after administration.

The morning of the test, four 1 gram tablets of the commercially available phenylbutazone were crushed in to a fine powder, and were added to one half gallon of grain with fourteen percent protein by lightly stifling for each horse. Each horse was given 15 minutes to consume the grain. None of the horses consumed their entire grain during this allotted time. Each of the five horses followed this procedure.

Two hours following administration a 4.5 cc blood sample was taken from each of the five horses. Thereafter, additional 4.5 cc blood samples were taken at half-hour intervals until the sixth hour. After the sixth hour 4.5 cc blood samples were taken hourly until the eighth hour. After the eighth hour 4.5 cc blood samples were taken at twelve and one-half hours, sixteen hours, and eighteen hours. The blood samples were taken with a 20 gauge one inch needle and promptly put into a green CST Lithium Heparin tubes and cooled in ice water at 36 degrees F. When each sample was collected, the blood sample was spun to separate the blood plasma from each sample. The separated blood plasma was placed in a freezer for twenty-four hours at 20 below zero.

After twenty-four hours, the blood plasma was thawed to room temperature and phenylbutazone levels were quantified for each sample by a validated HPLC method. The average phenylbutazone level for the five horses at each of the sampling time intervals are given in FIG. 1 as well as in the following chart.

The following chart illustrates the blood plasma concentrations achieved by Example 1 of the present invention as compared to pure phenylbutazone and to the prior art phenylbutazone composition shown in U.S. Pat. No. 6,022,563. This is instructive as the composition shown in U.S. Pat. No. 6,022,563 was similarly administered to the horses in an identical quantity as the present invention.

| Hours After Eating | Example 1 (NaHCO3) | U.S. Pat. No. 6,022,563 | Pure Phenylbutazone |
| --- | --- | --- | --- |
| 2 | 16.0 | 15.75 | 5.0 |
| 3 | 21.5 | 23.16 | 6.0 |
| 4 | 24.5 | 23.37 | 8.5 |
| 5 | 25.1 | 20.66 | 10.1 |
| 6 | 26.0 | 16.69 | 12.0 |
| 7 | 28.75 | 17.94 | 13.0 |
| 8 | 27.0 | 17.92 | 12.14 |
| 10 | 23.26 | 13.80 | 9.9 |
| 12 | 21.0 | 9.24 (at 12.5 hr) | 7.3 |
| 18 | 21.0 | 4.23 | 4.18 |

Example 2

Example 2 describes another preferred product formulation for the present invention, as well as the mixing and administration of the product.

The product formulation for Example 2 was prepared in a manner similar to that of Example 1 but containing calcium carbonate. The composition contained 100 kilograms of phenylbutazone, 4 kilograms of saccharine, 3 kilograms of Fresh Green Apple Flavor, 2 kilograms of Aspartame, 2 kilograms of calcium carbonate, and 4 kilograms of FloGard.

Bioequivalence Test

The formulation of Example 2 was tested for bioequivalency in a manner similar to that of Example 1 as follows. Three healthy mature geldings and two non-pregnant mares aged 3-15 years with similar weights were chosen to determine the blood plasma absorption of product mixture described above. Prior to the test, the horses did not receive any medication. The evening before the test, each horse was fed a normal meal which included of one gallon of grain and ten pounds of alfalfa hay. During the test each horse was stabled separately and had access to drinking water. On test day, each horse was fasted until given the phenylbutazone formulation. Each horse was later given a meal of one gallon of grain and ten pounds of alfalfa hay at five hours and at twelve and one-half hours after administration of the phenylbutazone formulation.

The morning of the test, 4.60 grams of the above phenylbutazone product (containing four grams of phenylbutazone) was added to one half gallon of grain. All five horses ate their grain during a 15 minute time period. 4.5 cc blood samples were taken from each of the five horses at 2, 3, 4, 5, 6, 7, 8, 10, 12, and 18 hours. The blood samples were promptly put into green CST Lithium Heparin tubes and cooled in ice water. When each sample was collected, the blood sample was spun to separate the blood plasma. The separated blood plasma was placed in a freezer for twenty-four hours at 20 below zero.

After twenty-four hours, the blood plasma was thawed to room temperature and phenylbutazone levels for each sample were measured by HPLC. The average phenylbutazone level for the five horses at each of the sampling time intervals are given in FIG. 1 as well as in the following chart.

The following chart illustrates the blood plasma concentrations achieved by Example 2 of the present invention as compared to pure phenylbutazone and to the prior art phenylbutazone composition shown in U.S. Pat. No. 6,022,563.

| Hours After Eating | Example 2 (CaCO3) | U.S. Pat. No. 6,022,563 | Pure Phenylbutazone |
| --- | --- | --- | --- |
| 2 | 16 | 15.75 | 5.0 |
| 3 | 22 | 23.16 | 6.0 |
| 4 | 25 | 23.37 | 8.5 |
| 5 | 25 | 20.66 | 10.1 |
| 6 | 26 | 16.69 | 12.0 |
| 7 | 29 | 17.94 | 13.0 |
| 8 | 27 | 17.92 | 12.14 |
| 10 | 23 | 13.80 | 9.9 |
| 12 | 21 | 9.24 (at 12.5 hr) | 7.3 |
| 18 | 21 | 4.23 | 4.18 |

The Example 2 composition containing phenylbutazone with calcium carbonate achieved blood plasma levels similar to those shown for phenylbutazone with sodium bicarbonate in Example 1. The phenylbutazone composition of Example 2 achieves blood plasma levels which are significantly higher than those achieved by prior phenylbutazone compositions which did not contain calcium carbonate, such as that shown in U.S. Pat. No. 6,022,563 to Gordon.

U.S. Pat. No. 6,022,563 discloses a formulation that provides slightly faster and more complete uptake than pure phenylbutazone when both are placed by tube directly into the horse's stomach. It can be observed that the present invention achieves a significantly higher and longer lasting blood concentration of phenylbutazone than the '563 composition, even through the testing of present invention relies on the horse to eat the composition while the '563 patent placed the entire dose into the horse via tube. The present testing results also show the dramatic improvement of the present invention as compared to requiring the horse to eat pure phenylbutazone. The horses discontinued eating and did not intake the full dose of phenylbutazone.

Additional compositions of a phenylbutazone formulation according to the present invention are provided here to illustrate the preferred ranges of the present invention. For example, a batch may contain 100 grams of phenylbutazone, 2 grams of green apple flavoring, 2 grams of anti caking agent, 4 grams of saccharine, 1 gram of aspartame, 2 grams of sucralose, and 2 grams of sodium bicarbonate or calcium carbonate.

Alternatively, an effective batch of medicine may also contain 100 grams of phenylbutazone, 4 grams of green apple flavoring, 2 grams of anti caking agent, 4 grams of saccharine, 1 gram of aspartame, 4 grams of sucralose, and 2 grams of sodium bicarbonate or calcium carbonate. These formulations are understood to perform equally to that disclosed above.

It is thus observed that the present invention preferably contains, for each 100 grams of phenylbutazone, between about 2 and 4 grams of flavoring, about 4 grams of saccharine, between about 1 and 2 grams of aspartame, between about 0 and 4 grams of sucralose, about 2 grams of sodium bicarbonate or calcium carbonate, and between about 2 and 4 grams of an anti caking agent. This results in a composition of between about 85.5 and 88.5 percent phenylbutazone, between about 1.8 and 3.4 percent flavoring, between about 3.4 and 3.5 percent saccharine, between about 0.8 and 1.7 percent aspartame, between about 0 and 3.4 percent sucralose, between about 1.7 and 1.8 percent sodium bicarbonate or calcium carbonate, and between about 1.7 and 3.5 percent anti caking agent. It will be appreciated that the percent composition may be trivially altered by adding inert ingredients to the above compositions without departing from the present invention.

FIG. 1 presents a chart illustrating the results of the bioequivalency tests discussed above. As is observed, the compositions of Example 1 and Example 2 achieved an approximate 250 percent increase in the blood plasma concentration of phenylbutazone as compared to phenylbutazone alone. Both of these results were based on the horse eating the medicine along with food. As discussed, the present invention, even when the horse is required to eat the medicine, achieved significant increases in both the intensity and duration blood phenylbutazone levels as compared to the prior art medicine disclosed in the '563 patent which was administered completely to the horse by tube. The inventor believes that this may be due to several factors. It is believed that the particular carrier formulation promotes the uptake of phenylbutazone into the horse, increasing not only the speed but also the efficiency of uptake. It is believed that both the particular combination of sweeteners, as well as the addition of sodium bicarbonate or calcium carbonate may thus improve the uptake of the phenylbutazone.

As the present formulation provides a significant increase in the blood plasma concentrations of phenylbutazone two desirable outcomes may be achieved. If a person doses the same amount of phenylbutazone to a horse, the resulting blood plasma levels will be higher and will last longer, improving the effectiveness of the medicine in treating the horse. Alternatively, if it is not desired to increase the resulting blood plasma levels, a lower dose may be provided to the horse while maintaining the same blood plasma levels. As phenylbutazone has been observed to cause some gastrointestinal discomfort or damage, this may reduce any such negative effects. Additionally, lowering the dose will reduce the cost and effort associated with treating a horse.

There is thus disclosed an improved phenylbutazone composition. It will be appreciated that numerous changes may be made to the present invention without departing from the scope of the claims.

What is claimed is:

1. A phenylbutazone carrier composition for promoting consumption and improving sustained bioavailability of phenylbutazone to horses comprising:
   a therapeutic dosage comprising 4 grams of phenylbutazone; and wherein the composition comprises, as a percentage of the weight of phenylbutazone:
   about 2 percent artificial flavor;
   about 3.5 percent saccharine;
   about 1 percent aspartame;
   about 2 percent sucralose; and
   about 2 percent of a carbonate salt or bicarbonate salt.

2. The composition of claim 1, wherein the salt comprises an alkaline earth carbonate.

3. The composition of claim 1, wherein the salt comprises calcium carbonate.

4. The composition of claim 1, wherein the salt comprises sodium bicarbonate.

5. The composition of claim 1, further comprising an anti-caking agent.

6. A phenylbutazone carrier composition for providing sustained duration bioavailability of phenylbutazone to horses comprising:
   a therapeutic dose comprising 4 grams of phenylbutazone; and
   a salt selected from the group consisting of carbonate salts and bicarbonate salts added to the phenylbutazone in an amount of about 2 percent of the weight of the phenylbutazone to improve bioavailability.

7. The composition of claim 6, wherein the salt comprises sodium bicarbonate.

8. The composition of claim 6, wherein the salt comprises an alkaline earth carbonate.

9. The composition of claim 6, wherein the salt comprises calcium carbonate.

10. The composition of claim 6, further comprising artificial sweetener.

11. The composition of claim 6, further comprising artificial flavor.

12. The composition of claim 6, wherein the composition comprises, as a percentage of the weight of phenylbutazone:
    about 4 percent saccharine;
    between about 1 and 2 percent aspartame;
    artificial flavoring; and
    anti-caking agent.

13. The composition of claim 12, wherein the composition further comprises, as a percentage of the weight of phenylbutazone, between about 2 and 4 percent sucralose.

14. A phenylbutazone carrier composition for improving consumption and providing extended duration bioavailability in animals comprising:
    phenylbutazone; and, for each 100 grams of phenylbutazone further comprising:
        about 2 grams of an alkaline earth metal carbonate salt or alkaline metal bicarbonate salt.

15. The composition of claim 14, further comprising artificial flavoring.

16. The composition of claim 14, further comprising anti caking agent.

17. The composition of claim 14, further comprising artificial sweetener.

18. The composition of claim 17, wherein the artificial sweetener comprises, for each 100 grams of phenylbutazone:
    between about 2 and 4 grams of sucralose;
    about 4 grams of saccharine; and
    between about 1 and 2 grams of aspartame.

19. The composition of claim 14, wherein the salt comprises, more specifically, an alkaline earth carbonate.

20. The composition of claim 14, wherein the salt comprises, more specifically, calcium carbonate.

* * * * *